United States Patent [19]

Kiesele et al.

[11] Patent Number: 5,076,904

[45] Date of Patent: Dec. 31, 1991

[54] ELECTROCHEMICAL MEASURING CELL FOR DETERMINING AMMONIA OR HYDRAZINE IN A MEASURING SAMPLE

[75] Inventors: Herbert Kiesele, Lübeck; Uwe Kühn, Wesenberg; Stephan Haupt, Lübeck, all of Fed. Rep. of Germany

[73] Assignee: Drägerwerk Aktiengesellschaft, Lübeck, Fed. Rep. of Germany

[21] Appl. No.: 507,755

[22] Filed: Apr. 12, 1990

[30] Foreign Application Priority Data

Apr. 29, 1989 [DE] Fed. Rep. of Germany ....... 3914284

[51] Int. Cl.⁵ .......................................... G01N 27/404
[52] U.S. Cl. ............................... 204/412; 204/153.14; 204/153.17; 204/415
[58] Field of Search .................... 204/415, 432, 153.14, 204/412

[56] References Cited

U.S. PATENT DOCUMENTS

| | | | |
|---|---|---|---|
| 3,649,505 | 3/1972 | Strickler et al. | 204/153.14 |
| 3,849,201 | 11/1974 | Kordesch | 204/412 X |
| 4,127,462 | 11/1978 | Blurton et al. | 204/432 X |
| 4,201,634 | 5/1980 | Stetter | 204/432 X |
| 4,599,157 | 7/1986 | Suzuki et al. | 204/415 X |

OTHER PUBLICATIONS

Ives et al., *Reference Electrodes, Theory and Practice*, Academic Press, New York, 1961, pp. 356–360.
Encyclopedia of Electrochemistry of the Elements, vol. 8, 1978, p. 413.

*Primary Examiner*—T. Tung
*Attorney, Agent, or Firm*—Walter Ottesen

[57] ABSTRACT

The invention is directed to an electrochemical measuring cell for determining ammonia or hydrazine in a gaseous or liquid measuring sample. The measuring cell has at least one measuring electrode and at least one counter electrode which are disposed in an electrolyte chamber filled with a soluble electrolyte. The electrolyte chamber is closed off in the direction facing toward the measuring sample by a permeable membrane. The measuring cell provides a selective ammonia measurement having the following advantages: a short response time, a linear response and a low tendency to drift. The electrodes of the measuring cell are so configured that the oxidation of the ammonia as a measurement reaction has no influence on the sensitivity of the measuring cell. For this purpose, at least the measuring electrode is provided with a coating containing cobalt oxide which is in direct contact with the electrolyte.

5 Claims, 1 Drawing Sheet

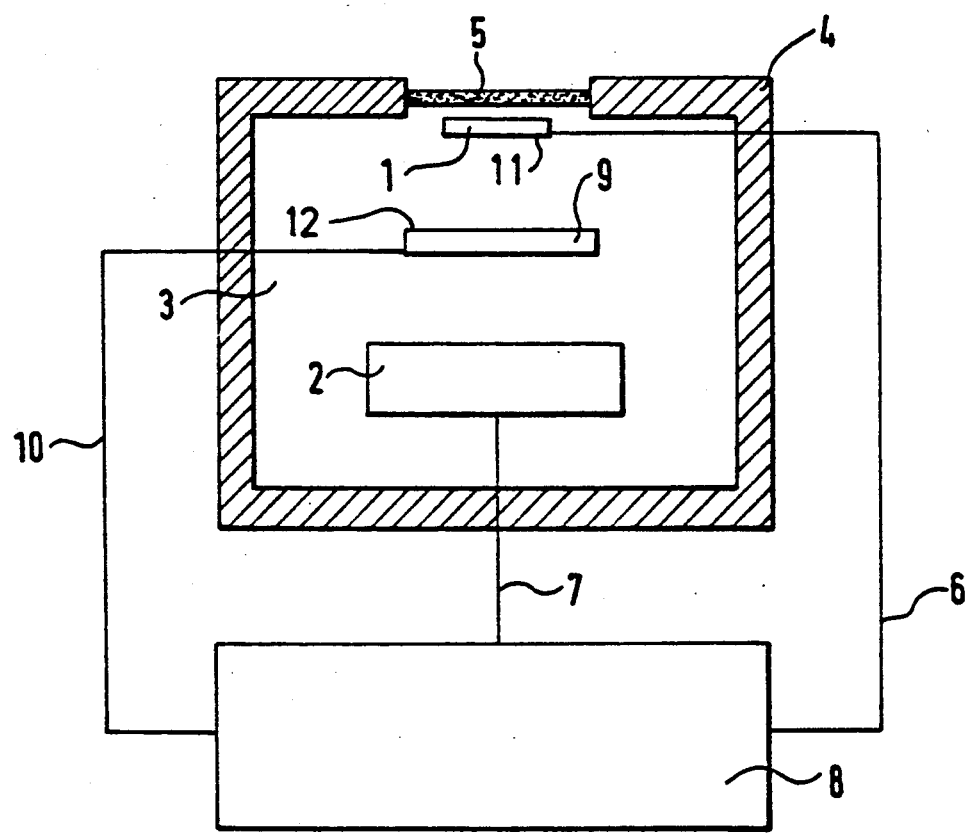

ELECTROCHEMICAL MEASURING CELL FOR DETERMINING AMMONIA OR HYDRAZINE IN A MEASURING SAMPLE

FIELD OF THE INVENTION

The invention relates to an electrochemical measuring cell for determining ammonia or hydrazine in a fluid (gaseous or liquid) measuring sample. The measuring cell has at least one measuring electrode and at least one counter electrode which are arranged in an electrolyte chamber filled with a soluble electrolyte. The electrolyte chamber is closed off with respect to the measuring sample by a permeable membrane.

BACKGROUND OF THE INVENTION

An electrochemical measuring cell of this kind is disclosed in U.S. Pat. No. 3,649,505 and includes a pH-electrode as a measuring electrode which is used to measure hydrogen ions. This potentiometric measurement of an ammonia concentration requires a long time duration for a completed measuring reaction. The long time duration is needed for the adjustment of an equilibrium. In this time duration, the $NH_3$ to be detected and the water content of the electrolyte conjointly form $NH_4OH$ which, in turn, dissociates into $NH^+_4$ ions and $OH^-$ ions. The slow step determining the speed for this reaction is the adjustment of the equilibrium with the gas space or the adjustment of the equilibrium at the glass membrane.

The glass electrode required for the pH-measurement changes in the characteristic of the glass membrane in the course of its use so that drift phenomena occur. A stable reference potential is necessary for carrying out the pH-measurement and a displacement of this reference potential in the course of use likewise leads to drift phenomena. The known measuring cell responds to all gases influencing the pH-value of the electrolyte so that its selectivity for measurements in corresponding gas mixtures is not adequate.

SUMMARY OF THE INVENTION

It is an object of the invention to provide an electrochemical measuring cell of the kind described above which is improved so that a selective ammonia measurement is obtained providing the following: short response time, a linear response and a low tendency to drift. It is a further object of the invention to provide such an electrochemical measuring cell having electrodes which are so configured that the oxidation of the ammonia or hydrazine as a measurement reaction has no influence on the sensitivity of this measuring cell.

The electrochemical measuring cell of the invention is for determining ammonia or hydrazine in a fluid measuring sample. The measuring cell includes: a housing having an opening directed toward the sample to be measured and defining an electrolyte chamber; a soluble electrolyte contained in the chamber; a permeable membrane mounted on the housing for closing off the chamber; a measuring electrode and a counter electrode disposed in the chamber so as to be in spaced relationship to each other; and, the measuring electrode having a coating containing cobalt oxide and the coating being formed on the measuring electrode so as to be in direct contact with the electrolyte.

The advantage of the invention is essentially that the oxidation of the ammonia at the measuring electrode is catalyzed by the cobalt oxide coating so that no disturbing secondary products develop at the measuring electrode which could hinder an oxidation which follows. Furthermore, no blocking of the electrode occurs because of an electrochemically inert passive layer.

The measuring cell according to the invention affords the advantage that it offers a very good long-term stability and negligible drift. Also, very high concentrations of ammonia can be measured because of the catalytically effective oxide layer. These high concentrations are rendered harmless with respect to catalytic poisons or disadvantageous influences of the electrolyte for the operational capability of the measuring cell. Because of the coating of cobalt oxide, the oxidation of ammonia at the measuring electrode surface occurs so rapidly that the ammonia concentration at this electrode surface is practically zero. This results in a high concentration gradient between the measuring sample and the surface of the measuring electrode. In this way, the measuring cell reaction is returned to a transport-controlled reaction without restrictive reaction steps. This leads to a rapid response time and to a high sensitivity of the measuring cell. Gold, platinum or iridium can be selected as a carrier material for the electrode. The measuring cell of the invention is equally well suited for detecting hydrazine.

For producing a cobalt oxide coating, a carrier material of gold defining the electrode can, for example, be dipped into a cobalt nitrate solution or a cobalt acetate solution and cobalt oxide is then electrically deposited thereon. Potassium nitrate can be added to the cobalt solution as a conductive electrolyte. Another method for forming the cobalt oxide coating is to form the carrier material for the electrode from a cobalt-containing alloy which is then oxidized.

Carrier materials for electrochemically measuring ammonia can be used by applying the coating containing cobalt oxide. Without this coating, a surface passivation in the form of a nitride formation occurs whereby the measuring sensitivity is reduced to the point that the measuring cell is unusable. In this connection, reference may be made to the "Encyclopedia of Electrochemistry of the Elements", Volume 8, 1978, page 413.

With respect to the measuring cell of the invention, it is emphasized that there is no cross-sensitivity against carbon monoxide or hydrogen.

In order to generate a reference potential for determining ammonia or hydrazine, a reference electrode is introduced into the measuring cell having a potential which functions as a reference point for the measurement. It is advantageous to likewise provide such a reference electrode with a coating containing cobalt oxide. A measuring cell of this kind affords the advantage that it can be stored with short-circuited electrodes whereby it is immediately operationally ready because of the short warm-up time. Furthermore, the dependency of the residual current on temperature is minimized since the potential of the measuring electrode and of the reference electrode are influenced in the same manner by the temperature.

BRIEF DESCRIPTION OF THE DRAWING

The invention will now be described with reference to the single figure of the drawing which is a side elevation view, in section, of a measuring cell according to an embodiment of the invention.

DESCRIPTION OF THE PREFERRED EMBODIMENTS OF THE INVENTION

The electrochemical measuring cell includes an electrolyte 3 in which a measuring electrode 1, a counter electrode 2 and a reference electrode 9 are introduced. The electrodes (1, 9) have respective coatings (11, 12) containing cobalt oxide. The electrolyte 3 is closed off in a direction facing toward the measuring sample by a membrane 5 which is permeable to ammonia and which is attached to the housing 4 in a seal-tight manner. The measuring electrode 1, the counter electrode 2 and the reference electrode 9 have respective measurement leads (6, 7, 10) which are passed through the housing 4 and connected to an evaluation device 8 for processing the measurement signals.

It is understood that the foregoing description is that of the preferred embodiments of the invention and that various changes and modifications may be made thereto without departing from the spirit and scope of the invention as defined in the appended claims.

What is claimed is:

1. An electrochemical measuring cell for determining ammonia or hydrazine in a fluid measuring sample, the measuring cell comprising:
    a housing having an opening directed toward the sample to be measured and defining an electrolyte chamber;
    a soluble electrolyte contained in said chamber;
    a permeable membrane mounted on said housing for closing off said chamber;
    a measuring electrode and a counter electrode disposed in said chamber so as to be in spaced relationship to each other;
    said measuring electrode having a coating containing cobalt oxide and said coating being formed on said measuring electrode so as to be in direct contact with said electrolyte; and,
    a reference electrode disposed in said electrolyte and having a coating formed thereon which contains cobalt oxide.

2. The electrochemical measuring cell of claim 1, said measuring electrode and said reference electrode each including a carrier made of a noble metal and said coating being electrolytically deposited on said carrier.

3. The electrochemical measuring cell of claim 1, said measuring electrode and said reference electrode each including a carrier made of an alloy containing cobalt and said coating being an oxide layer formed by oxidizing said alloy.

4. An electrochemical measuring cell for determining ammonia or hydrazine in a fluid measuring sample, the measuring cell comprising:
    a housing having an opening directed toward the sample to be measured and defining an electrolyte chamber;
    a soluble electrolyte contained in said chamber;
    a permeable membrane mounted on said housing for closing off said chamber;
    a measuring electrode and a counter electrode disposed in said chamber so as to be in spaced relationship to each other;
    said measuring electrode having a coating containing cobalt oxide in direct contact with said electrolyte;
    said coating being formed on said measuring electrode by an electrolytic deposition on said measuring electrode; and,
    a reference electrode disposed inn said electrolyte and having a coating formed thereon which contains cobalt oxide.

5. The electrochemical measuring cell of claim 4, said measuring electrode including a carrier made of a noble metal and said coating being electrolytically deposited on said carrier.